(12) United States Patent
Arber et al.

(10) Patent No.: US 9,700,741 B2
(45) Date of Patent: Jul. 11, 2017

(54) IMAGE GUIDED RADIATION THERAPY APPARATUS

(71) Applicant: Elekta AB (Publ), Stockholm (SE)

(72) Inventors: Philip Lee Arber, West Sussex (GB); Joseph Hubert Marie Habets, Oirsbeek (NL); Clifford William Perkins, West Sussex (GB)

(73) Assignee: Elekta AB (Publ), Stockholm (SE)

( * ) Notice: Subject to any disclaimer, the term of this patent is extended or adjusted under 35 U.S.C. 154(b) by 162 days.

(21) Appl. No.: 14/524,643

(22) Filed: Oct. 27, 2014

(65) Prior Publication Data
US 2015/0119693 A1 Apr. 30, 2015

(30) Foreign Application Priority Data
Oct. 28, 2013 (GB) .................................. 1319029.3

(51) Int. Cl.
*A61N 5/10* (2006.01)

(52) U.S. Cl.
CPC ......... *A61N 5/1081* (2013.01); *A61N 5/1067* (2013.01); *A61N 2005/1055* (2013.01); *Y10T 29/49616* (2015.01)

(58) Field of Classification Search
CPC .......... A61N 2005/1055; A61N 5/1067; A61N 5/1081; Y10T 29/49616
See application file for complete search history.

(56) References Cited

U.S. PATENT DOCUMENTS

| 4,912,735 A | * | 3/1990 | Beer ....................... A61B 6/035 378/15 |
| 2004/0022350 A1 | * | 2/2004 | Gregerson ............. A61B 6/032 378/15 |
| 2007/0074373 A1 | * | 4/2007 | Herring ................ H05K 5/0226 16/260 |
| 2007/0143960 A1 | * | 6/2007 | Schluter .................. E05D 7/105 16/260 |
| 2011/0301449 A1 | * | 12/2011 | Maurer, Jr. ............. A61B 6/032 600/411 |
| 2013/0006091 A1 | * | 1/2013 | Manjeshwar .......... A61B 6/037 600/411 |

FOREIGN PATENT DOCUMENTS

| WO | WO 03/008986 A2 | 1/2003 |
| WO | WO 2004/004829 A1 | 1/2004 |

OTHER PUBLICATIONS

GB Search Report, issued in corresponding Application No. GB 1319029.3, dated May 22, 2014, one (1) page.

* cited by examiner

*Primary Examiner* — Katherine Fernandez
(74) *Attorney, Agent, or Firm* — Finnegan, Henderson, Farabow, Garrett & Dunner LLP

(57) ABSTRACT

A radiation therapy apparatus includes a radiation source and a ring shaped gantry. The gantry includes a static ring component and a dynamic ring component upon which the radiation source is mounted, the dynamic ring component is rotatable about its center and is provided in multiple arcuate parts that can be assembled together to form the dynamic ring component.

15 Claims, 4 Drawing Sheets

IMAGE GUIDED RADIATION THERAPY APPARATUS

CROSS REFERENCE TO RELATED APPLICATION

The present application claims the benefits of priority to GB 1319029.3, filed on Oct. 28, 2013. The entire content of this application is incorporated herein by reference.

FIELD OF THE INVENTION

The present invention relates to image guided radiation therapy (IGRT) apparatus. More particularly the invention provides an IGRT apparatus which is conveniently transportable.

BACKGROUND OF THE INVENTION

Radiation therapy is a localised treatment designed to treat an identified tissue target (such as a cancerous tumour) and spare the surrounding normal tissue from receiving doses above specified tolerances thereby minimising risk of damage to healthy tissue. Prior to delivery of radiation therapy, an imaging system can be used to provide a three dimensional image of the target from which the target's size and mass can be estimated and an appropriate treatment plan determined.

Many factors may contribute to differences between the dose distribution determined in the treatment plan and the delivered dose distribution. One such factor is an inconsistency between the patient position at the imaging stage and the patient position in the radiation treatment unit.

Image guided radiation therapy (IGRT) is known. The method involves the use of an imaging system to view target tissues whilst radiation treatment is being delivered to the target tissue. IGRT incorporates imaging coordinates from the treatment plan to ensure the patient is properly aligned for treatment in the radiation therapy device.

Various medical imaging technologies are used to identify target tissues in radiation therapy planning and IGRT. These include (without limitation); Computed Tomography (CT), Positron Emission Tomography (PET), ultrasound imaging and Magnetic Resonance Imaging (MRI).

The Applicant's prior published international patent application no WO03/008986 describes a device for use in IGRT which includes the functions of an MRI device in a radiation therapy treatment apparatus and proposes technology for overcoming the problems in doing so. The device comprises a large ring gantry onto which a linear accelerator is mounted and arranged to travel around a target positioned at the isocentre of the ring. An MRI sits in the aperture of the ring gantry sharing the isocentre. A body to be treated is introduced into a treatment space at the isocentre by means of a sliding table.

The large scale of these combined devices will be appreciated. In order to accommodate the imaging component within the radiation therapy component, the gantry in such devices is typically of the order of 2-3 meters in diameter and a considerable weight. It will be appreciated such equipment cannot be easily transported or manoeuvred.

SUMMARY OF THE INVENTION

In accordance with the present invention there is provided a radiation therapy apparatus comprising a radiation source, such as a linear accelerator or radioisotope source, and a ring shaped gantry, wherein the gantry comprises a static ring component and a dynamic ring component upon which the radiation source is mounted, the dynamic ring component being rotatable about the ring centre and being provided in multiple arcuate parts which can be assembled together to form the dynamic ring component.

Desirably the apparatus is an image guided radiation therapy (IGRT) apparatus comprising a medical imaging device and a radiation source.

The inventors have recognised that the cumbersome proportions of a combined medical imaging and radiation therapy treatment device present a challenge in transporting the device and in accessing existing buildings into which the apparatus is to be installed. The largest component is the dynamic ring of the gantry which typically has a diameter of 2-3 meters, along with a significant depth and weight. By reducing the dynamic ring into multiple arcuate parts, the maximum dimension and weight of the individual parts is significantly reduced compared to a full ring and the apparatus becomes easier to transport and deliver into existing buildings.

In a simple example, the dynamic ring is provided in two arcuate parts. The parts may be of substantially equal size or of different size. In a preferred embodiment the dynamic ring is provided in three arcuate parts of substantially equal length. The dynamic ring may be provided in more than three arcuate parts. It will be appreciated that the assembled ring must have a consistent diameter and present a flat surface for interfacing with a bearing ring provided on the static ring component against which the dynamic ring can be rotated. These requirements present a practical limitation to the number of arcuate parts into which the dynamic ring can usefully be provided.

Preferably, the dynamic ring comprises an odd number of arcuate parts.

Preferably, the interfaces at which the arcuate parts meet are provided in an offset configuration. Put another way, they are not positioned opposite one another.

Preferably, the dynamic ring comprises an odd number of arcuate parts each of substantially the same size.

Where the arcuate parts comprise more than two in number, the parts will each be marked to identify their position in the assembled ring. The assembly further comprises connectors for connecting the arcuate parts to form a ring and means for fixing their position in the assembled ring. The fixing means may be separate components, alternatively the connectors may serve as the fixing means.

Desirably the connectors allow for adjustment of the separation between adjacent arcuate parts within a defined tolerance. Known mechanical connectors can be used, for example, the connectors may comprise one or more damps for holding adjacent surfaces of two arcuate parts together. In an embodiment, the connectors comprise bolts sized to pass through aligned bores in adjacent ends of two arcuate parts. Desirably at least two such bolts are provided between the adjacent ends, a first bolt sized to pass through aligned bores near a front face of the dynamic ring and a second bolt arranged to pass through aligned bores near a rear face of the assembled ring.

In a preferred embodiment, a peg is provided to pass through a bore defined when two adjacent ends of two arcuate pieces are aligned; this bore extends in a longitudinal direction of the ring, substantially orthogonal to the bores through which the bolts pass. The peg includes an aperture. When properly assembled, a bolt passes through the aperture as well as the aligned bores of the adjacent arcuate pieces.

Connectors are desirably provided near an outer circumference of the assembled dynamic ring and near an inner circumference of the assembled dynamic ring. The connectors may include shim plates to be located radially from the inner circumference of the assembled dynamic ring to assist in maintaining roundness of the ring. The shim plates may be selectively dimensioned to fit between specified surfaces of adjacent arcuate pieces. The shim plates may be marked to identify their proper position in the assembled dynamic ring. The shim plates incorporate apertures and are held in the assembly by connector bolts passing through these apertures.

Also provided by the present invention is a method for assembling a gantry of a radiation therapy apparatus according to any preceding claim comprising;
to an in situ static structure on which a bearing mount is provided, add the multiple arcuate parts to the assembly in sequence as follows;
 a) hold the first arcuate part in position,
 b) secure the first arcuate part to the bearing mount,
 c) rotate the assembly through at least a length of the first arcuate part,
 d) repeat steps a) to c) for the second part,
 e) connect the second arcuate part to the first arcuate part by means of suitable connectors,
 f) rotate the assembly through at least a length of the second part,
 g) repeat steps a) to f) for all subsequent arcuate parts until a complete dynamic ring is assembled,
 h) check alignment of the assembled dynamic ring,
 i) make adjustments to the positioning of the arcuate parts as appropriate by adjusting the connectors until the alignment is satisfactory.

Preferably, prior to step (h), the connectors are hand tight and the dynamic ring is allowed to rotate.

A hoist may be used to position each arcuate part in place.

The multi-part dynamic ring is assembled to an in situ static ring on which is provided a bearing mount. The arcuate parts can be added to the assembly in sequence first held in position by a supporting hoist. With the hoist still bearing the weight of the arcuate part, the arcuate part is secured to the bearing mount using conventional fastening components and methods. The hoist can then be detached. The assembly is rotated, desirably through at least a length of the arcuate part. After the second arcuate part is mounted to the bearing mount, the adjacent arcuate parts are connected by suitable connectors, for example (but without limitation) the bolts, pegs and shim plates described above. With the parts connected, the assembly is again rotated. Subsequent arcuate parts are added to the assembly in a similar manner until the dynamic ring is finally assembled. Initially, connectors are hand tightened. In a hand tightened state, the arcuate parts are permitted to move axially with respect to each other. Put another way, the arcuate parts are permitted to slide past each other at their interfaces in an axial direction. The alignment of the static ring facing surface of each of the arcuate parts is assisted through rotation of the fully assembled dynamic ring.

Tolerances are provided to allow for further, minor adjustments using tooling to ensure the arcuate parts are properly aligned.

The circumferential and planar alignment of the arcuate parts is checked and individual connectors adjusted until the alignment is satisfactory. Once alignment is satisfactory, the connectors are further tightened to maintain the alignment.

BRIEF DESCRIPTION OF DRAWINGS

An embodiment of the invention will now be described with reference to the accompanying Figures in which.

DETAILED DESCRIPTION OF DRAWINGS

Figure 1:
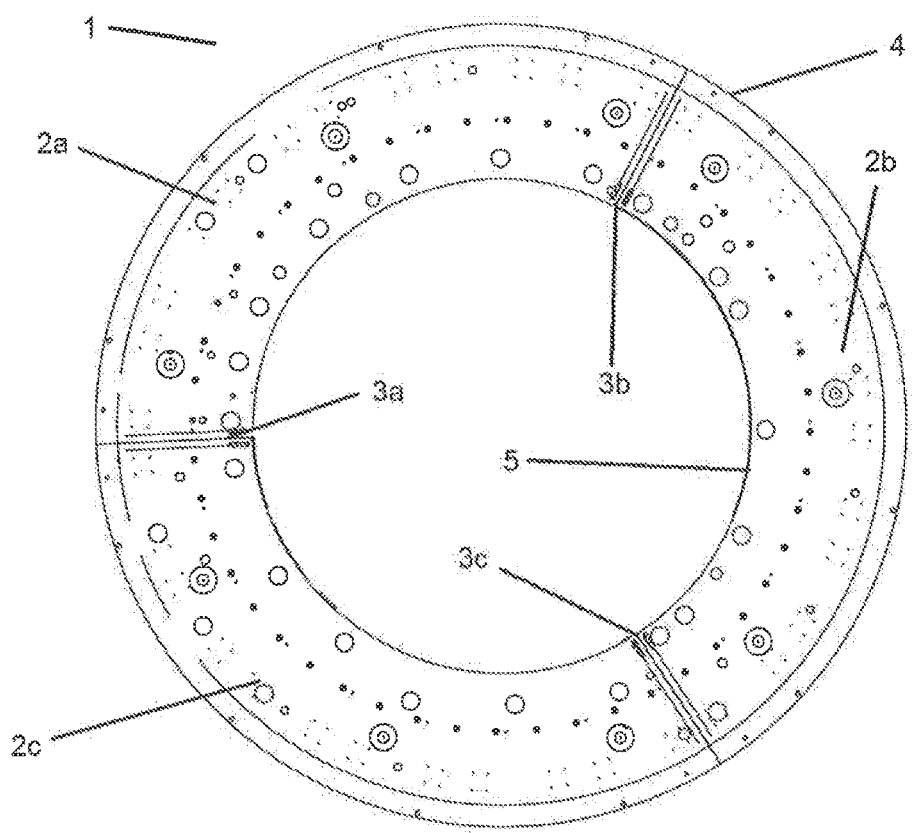
FIG. 1 shows a dynamic ring of a gantry of a radiation therapy apparatus in accordance with an embodiment of the invention.

FIG. 1 shows a dynamic ring component 1 of a gantry for an apparatus in accordance with the invention. As can be seen, the dynamic ring is composed of three similar arcuate parts 2a, 2b, 2c which connect together at interfaces 3a, 3b and 3c to form a ring having an outer circumference 4 and an inner circumference 5.

Figure 2:
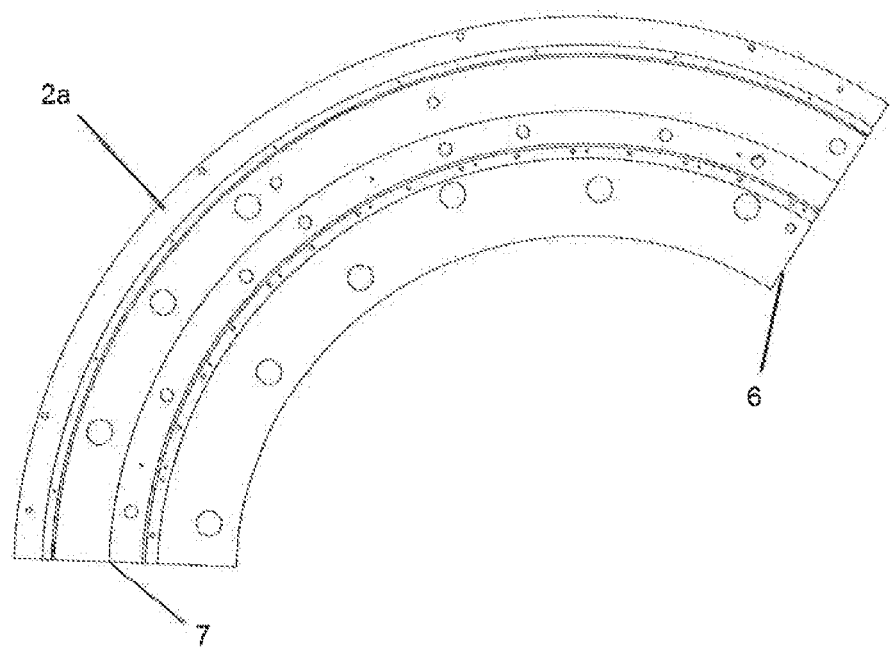
FIG. 2 shows one arcuate part of the dynamic ring of FIG. 1.

FIG. 2 shows one of the three parts 2a, in isolation. As can be seen the arcuate part has two connecting ends 6 and 7.

Figure 3A:
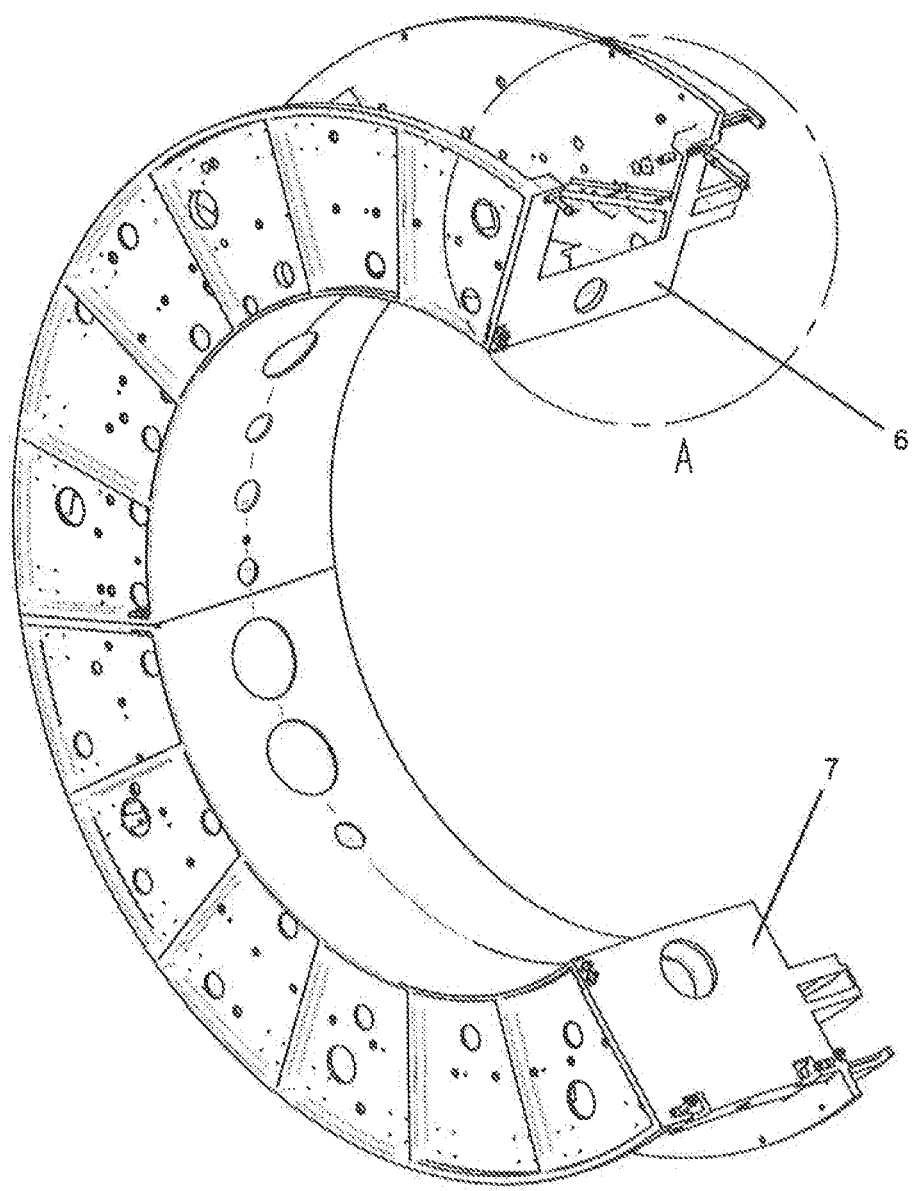
FIG. 3A shows the arcuate part of FIG. 2 in a perspective view revealing detail of the connecting ends of the part.

FIG. 3A shows the arcuate part of FIG. 2 in a perspective view revealing detail of the shapes and features of connecting ends 6 and 7.

Figure 3B:
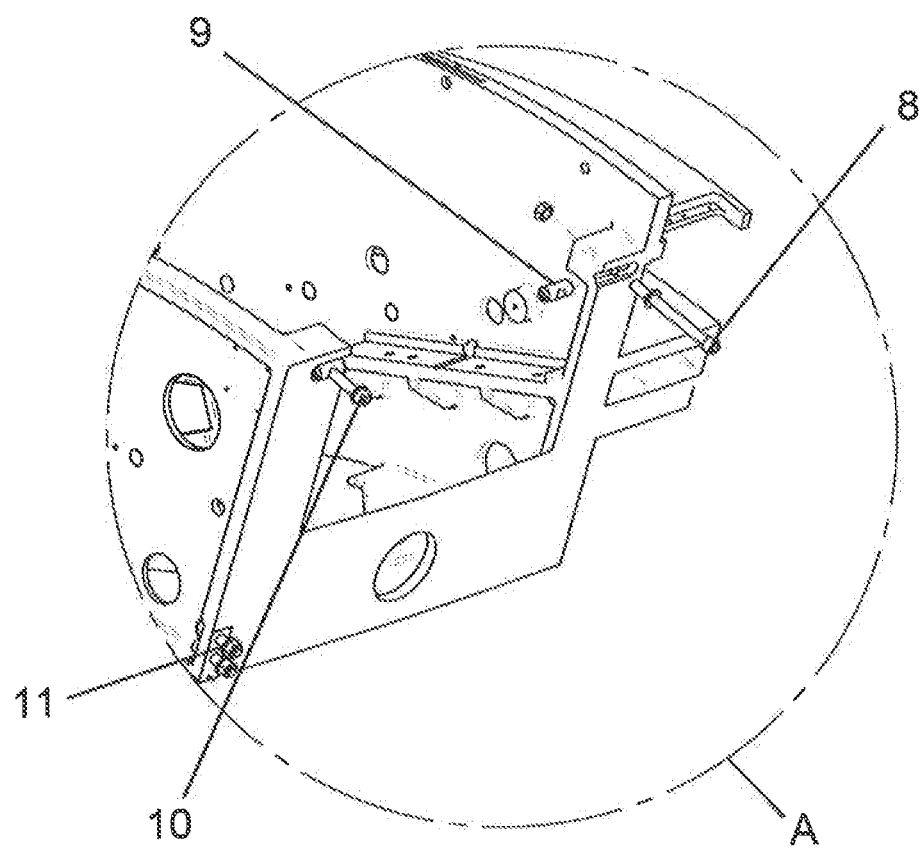
FIG. 3B shows a more detailed view of one end of the arcuate part shown in FIG. 3A with connectors positioned for assembly of two adjacent arcuate parts.

FIG. 3B shows end 6 of FIG. 3A in closer detail. As can be seen, near to the outer circumference 4 and inner circumference 5 of the arcuate part, are provided connector bores which are aligned for assembly of adjacent arcuate parts. Bolts 3 and 10 pass through the aligned bores and on securing of nuts to the bolts, the adjacent arcuate parts are connected to one another. Adjacent the outer circumference 4 a bore is defined when two adjacent ends of two arcuate pieces are aligned. This bore extends in a longitudinal direction of the ring, substantially orthogonal to the bores through which the bolts 8 and 10 pass. A peg 9 is received in the bore. The peg 9 has an aperture through which bolt 8 is threaded.

It can be seen the bolts 8 and 10 are positioned near a front face of the arcuate part. Additional connector bolts 11 pass through additional aligned holes near a rear face of the arcuate part. A shim plate (not shown) may be inserted at an interface 3a, 3b, 3c between adjacent ends of the arcuate portions. Bolts 10 and 11 near the inner circumference 5 can be passed through apertures in the shim plates to secure the shim plates in position.

The arrangement of pegs and bores is configured such that, when the bolts are hand tightened, the arcuate parts are permitted to move past each other in an axial direction.

Other embodiments and simple design variations of the embodiments disclosed herein will no doubt occur to the skilled addressee without departing from the true scope of the invention as defined in the appended claims.

The invention claimed is:
1. A radiation therapy apparatus comprising:
 radiation source configured to emit radiation;
 a first connector bolt:
 a second connector bolt:
 a peg comprising an aperture: and
 a ring-shaped gantry including:
  a static ring component having a bearing mount; and
  a dynamic ring component upon which the radiation source is mounted, the dynamic ring component being rotatable about its center and including multiple arcuate parts assembled together to form the dynamic ring component, at least one of the arcuate parts being secured to the bearing mount of the static ring component, the arcuate parts comprising bores which align when the dynamic ring component is assembled, wherein:
  a first pair of aligned bores near a front face of the dynamic ring component is configured to receive the first connector bolt;
  a second pair of aligned bores near a rear face of the dynamic ring component is configured to receive the second connector bolt;
  the ends of the arcuate parts define at least one additional bore when two adjacent ends of two arcuate pieces are aligned, the at least one additional bore extending in a longitudinal direction of the dynamic ring component substantially orthogonal to the first and second pairs of aligned bores; and
  the at least one additional bore is configured to receive the peg, the peg receiving at least one of the first or second connector bolts through the aperture.

2. The radiation therapy apparatus as claimed in claim 1, wherein the radiation therapy apparatus is an image guided radiation therapy apparatus comprising a medical imaging device.

3. The radiation therapy apparatus as claimed in claim 2, wherein the medical imaging device is a Magnetic Resonance Imaging (MRI) device.

4. The radiation therapy apparatus as claimed in claim 1, wherein the multiple arcuate parts are of equal size.

5. The radiation therapy apparatus as claimed in claim 4, wherein the dynamic ring component comprises three arcuate parts.

6. The radiation therapy apparatus as claimed claim 1, wherein the multiple arcuate parts are different sizes.

7. The radiation therapy apparatus as claimed in claim 1, wherein the first and second connector bolts are sized to fit through the first and second pair of aligned bores.

8. The radiation therapy apparatus as claimed in claim 1, further comprising at least one shim plate configured to be located radially from the inner circumference of the assembled dynamic ring component.

9. The radiation therapy apparatus as claimed in claim 8, wherein the at least one shim plate includes an aperture for receiving at least one of the first or second connector bolts to hold the at least one shim plate in position between adjacent end surfaces of two arcuate pieces.

10. The radiation therapy apparatus as claimed in claim 1, wherein the multiple arcuate parts are marked to identify their proper position and/or orientation in the dynamic ring component.

11. The radiation therapy apparatus as claimed in claim 1, wherein the radiation source comprises a linear accelerator.

12. The radiation therapy apparatus as claimed in claim 1, wherein the radiation source comprises a radioisotope source.

13. The radiation therapy apparatus as claimed in claim 1, wherein the assembled dynamic ring component has a consistent diameter throughout the dynamic ring component.

14. An image-guided radiation therapy apparatus, comprising:
  a medical imaging device;
  a radiation source configured to emit radiation; and
  a ring-shaped gantry comprising;
    a static ring component having a bearing mount; and
    a dynamic ring component upon which the radiation source is mounted, wherein:
      the dynamic ring component is rotatable about its center;
      the dynamic ring component includes multiple arcuate parts assembled together to form the dynamic ring component, the arcuate parts comprising bores which align when the dynamic ring component is assembled, a first pair of aligned bores near a front face of the dynamic ring component configured to receive a first connector bolt, and a second pair of aligned bores near a rear face of the dynamic ring component configured to receive a second connector bolt;
      the ends of the arcuate parts define at least one additional bore when two adjacent ends of two arcuate pieces are aligned, the at least one additional bore extending in a longitudinal direction of the dynamic ring component substantially orthogonal to the first and second pairs of aligned bores;
      the at least one additional bore is configured to receive a peg comprising an aperture, the peg receiving at least one of the first or second connector bolts through the aperture;
      the assembled dynamic ring component has a consistent diameter, throughout the dynamic ring component; and
      at least one of the arcuate parts is secured to the bearing mount of the static ring component.

15. The image-guided radiation therapy apparatus as claimed in claim 14, wherein the medical imaging device is a Magnetic Resonance Imaging (MRI) device integrated with the radiation therapy apparatus.

* * * * *